United States Patent [19]  [11] 4,147,606
Golias [45] Apr. 3, 1979

[54] CLINICAL PROCEDURE FOR MEASURING LIPOPROTEIN TRIGLYCERIDES

[75] Inventor: Tipton L. Golias, Beaumont, Tex.

[73] Assignee: Helena Laboratories Corporation, Beaumont, Tex.

[21] Appl. No.: 928,049

[22] Filed: Jul. 26, 1978

Related U.S. Application Data

[63] Continuation-in-part of Ser. No. 835,387, Sep. 21, 1977, Pat. No. 4,105,521.

[51] Int. Cl.$^2$ .................. G01N 27/26; G01N 33/16
[52] U.S. Cl. .................. 204/180 S; 204/180 G; 204/299 EC; 424/12; 23/230 B
[58] Field of Search .......... 204/180 G, 180 S, 180 R, 204/299; 424/12; 23/230 B

[56] References Cited

U.S. PATENT DOCUMENTS

| | | | |
|---|---|---|---|
| 3,808,118 | 4/1974 | Golias | 204/299 |
| 3,873,433 | 3/1975 | Seidel et al. | 204/180 S X |
| 4,041,021 | 8/1977 | Bohn | 424/12 |
| 4,094,759 | 6/1978 | Ruhenstroth-Bauer et al. | 204/180 G |

Primary Examiner—Arthur C. Prescott
Attorney, Agent, or Firm—Cullen, Sloman, Cantor, Grauer, Scott & Rutherford

[57] ABSTRACT

An electrophoresis method of determining the concentration of high density lipoprotein (HDL) triglycerides in fluids, for example, body fluids and simultaneously determining the concentration of very low density lipoprotein (VLDL) and low density lipoprotein (LDL) triglycerides in the fluid. The method includes applying a small sample of the fluid to an electrophoresis support medium, applying a direct current across the medium, applying a developing substrate to the electrophoresed lipoproteins and quantitatively determining the concentration of each lipoprotein triglyceride. This method does permit direct and simultaneous measurement of each lipoprotein triglycerides fraction while eliminating precipitation of each fraction as required by the prior art.

12 Claims, No Drawings

CLINICAL PROCEDURE FOR MEASURING LIPOPROTEIN TRIGLYCERIDES

RELATED APPLICATION

This application is a continuation-in-part application of my copending application for U.S. Pat., Ser. No. 835,387, filed Sept. 21, 1977, now U.S. Pat. No. 4,105,521.

FIELD OF THE INVENTION

The present invention relates to a clinical method of determining the concentration of lipoprotein triglyceride fractions, particularly high density lipoprotein (HDL) triglycerides in serum, plasma and other body fluids. My above referenced co-pending application discloses a method of determining the lipoprotein cholesterol density fractions using a similar method.

Blood serum triglycerides have been recognized for over ten years as associated with coronary artery diseases. Medical experts have long believed that persons having elevated serum triglyceride levels are more likely to suffer myocardial infarcation (heart attack) than persons having lower levels of triglycerides. However, the correlation between triglyceride levels and coronary artery disease is not consistent and therefore the present diagnostic tests for triglyceride are considered advisory only and not a reliable indicator of the likelihood of myocardial infarcation or premature coronary artery disease.

The more recent work by the National Heart, Lung and Blood Institute of Bethesda, Maryland and the Framingham Heart Institute of Framingham, Massachusetts has suggested that one fraction of cholesterol, high density lipoprotein, is actually a "predictor of inverse cardiovascular risk". This discovery should improve our understanding of the role of cholesterol in coronary artery diseases. Further, a correlation between lipoprotein triglyceride fractions and cardiovascular risk may also be found. Therefore, a simple fast and reliable test for the concentrations of lipoprotein triglyceride fractions in body fluids is necessary. The Nation Institute of Health has also worked with triglycerides as an indicator of the risk of coronary disease as set forth above.

The present clinical tests for determining the concentration of high density lipoprotein (HDL) triglyceride in body fluid requires precipitation of the other triglyceride (low density and very low density lipoproteins) and determination of the triglyceride concentration in the supernate. Briefly, the recommended test includes adding heparin solution to the fluid sample and mixing, adding manganese chloride and mixing, chilling and drawing off the supernate. All of the triglyceride remaining in the supernate is assumed to be high density lipoprotein triglyceride. The triglyceride is extracted with isopropanol and the extract assayed for triglyceride in spectrophotometers or continuous-flow analyzers.

It will be apparent that this procedure has several disadvantages. The procedure is slow and therefore expensive. Because precipitation is used, the reliability of the test is suspect. Finally, the assumption that all of the triglyceride remaining after precipitation is high density lipoprotein has been seriously questioned. The problem with this assumption is the lack of specificity of the commonly used cations, specifically $Ca^{2+}$, $Mg^{2+}$ and $Mn^{2+}$, in the lipoprotein-heparin interaction. Further, it has been found that subclasses of high density lipoproteins can be precipitated in the presence of manganese cations. Thus, the precipitation method may not be as reliable as believed.

The method of determining the concentration of lipoprotein triglyceride fractions of the present invention eliminates these problems and provides a simple and reliable clinical procedure.

SUMMARY OF THE INVENTION

Triglyceride occurs in blood serum bound to serum proteins along with other lipids (i.e., cholesterols, phospholipids, et cetera) to form lipoproteins. These lipoproteins occur in different densities as initially determined by ultracentrifugation. The density fractions are generally referred to as high density lipoproteins (HDL), very low density lipoprotein (VLDL) and low density lipoproteins (LDL). It will be understood that further fractions have been identified including subclasses of HDL however these are the principal features.

Although certain proteins have been separated by electrophoresis methods, such methods have not been successful in separating smaller molecules such as triglycerides. The method of this invention takes advantage of the fact that triglycerides are bound to serum proteins, permitting separation by electrophoresis methods. As described, the method of this invention permits simultaneous determination of the concentrations of high density lipoprotein, very low density lipoprotein and low density lipoprotein triglycerides in body fluids such as serum, plasma, etc. The procedure is as follows.

As set forth in my above referenced prior copending application, it was first discovered that the density fractions of lipoprotein cholesterols could be separated and quantitatively determined by electrophoresis techniques. It has now been discovered that a similar method may be used to simultaneously determine the density fractions of triglycerides as set forth in the following method.

First, a small sample of the body fluid to be tested is applied to a solid electrophoresis support media, preferably cellulose acetate. The support media will generally be in the form of a strip. Next, a direct current is applied across the support media for a predetermined time to separate the high density, very low density and low density lipoprotein triglycerides on the media. Next, a developing substrate sensitive to small concentrations of triglyceride is applied to the electrophoresed lipoprotein triglyceride, developing the separated lipoprotein triglyceride on the support media, the triglycerides appearing reddish in color. Finally, the concentrations of each of the lipoprotein triglycerides may be quantitatively determined by one or any of several methods, including direct densitometry or by eluting each fraction and measuring the concentration of each lipoprotein in the eluate.

The method of the present invention thus permits simultaneous measurement of high density lipoprotein triglycerides, low density lipoprotein triglyceride and very low density lipoprotein triglyceride. The procedure is faster and less costly than the present clinical methods because the procedure of the present invention eliminates precipitation. Finally, the method of the present invention is more reproducible because the determination of the lipoprotein triglyceride concentrations are made directly from the entire sample. Other advantages and meritorious features of the present invention will be more fully understood from the following detailed description.

DETAILED DESCRIPTION OF THE METHOD OF THIS INVENTION

The method of determining concentrations of lipoprotein triglycerides of this invention is basically an electrophoretic determination. Thus, a small sample of the body fluid to be tested is first applied to a solid electrophoresis support media, preferably cellulose acetate. A suitable cellulose acetate support media is available in strip form from the assignee of the present invention under the trade name "Titan III". It will be understood that other support media including cellulose nitrate, agar, agarose, paper, acrylamide gel, cellulose, silica gel, starch gel, etc. may also be used. The fluid sample is preferably applied to the support media in a straight line, permitting accurate reading following electrophoresis. A suitable apparatus for applying the fluid sample to the support media is disclosed in U.S. Pat. No. 4,006,705.

Next, a direct electric current is applied across the media, causing separation of the lipoprotein triglyceride fractions. Movement of the lipoprotein triglycerides through a medium such as celulose acetate depends upon the medium, the intensity of the electric field, the time and the character of the charged particle. In view of the fact that these variables will be constant for each lipoprotein triglyceride fraction, the fractions are separated upon application of the electric field. It has been found that optimum separations for lipoprotein triglyceride occur at about one hundred eighty (180) volts (DC) for about twenty minutes. It has been found that the order of separation is HDL, VLDL and LDL triglyceride, which is the order given herein.

Following electrophoresis, a developing substrate sensitive to small concentrations of triglyceride is applied to the electrophoresed lipoprotein triglyceride strip. In the preferred embodiment, the developing substrate is an enzymatic triglyceride reagent such as available from Dow Diagnostics, Indianapolis, Ind. The preferred enzymatic triglyceride reagent available from Dow Diagnostics has the following composition:

| Concentration | Ingredient |
| --- | --- |
| 0.3 mg | Magnesium Chloride (MgCl$_2$) |
| 1.8 mg | Adenosine-5'-Triphosphate (ATP) |
| 7.2 mg | Nicotinamide adenine dinucleotide (NAD) |
| 0.25 mg | 2-(p-iodophenyl)-3-p-5-phenyltetrazolium chloride (IN) |
| 5.52 u (activity units)/test | Diaphorase |
| 0.92 u/test | Glycerol Kinase |
| 13.8 u/test | Glycerol-1-phosphate dehydrogenase |
| 100 u/test | Lipases |

The lyphylized sample is diluted in 1 ml. of a buffer having a pH 7.6.

In the method of the present invention, the electrophoresed lipoprotein triglycerides are incubated with the triglyceride substrade for about fifteen minutes at 37° Centigrade. The developing substrate may be applied to the electrophoresed triglycerides by one of several methods, including simply soaking or submerging the support media in the reagent or, more preferably, sandwiching the support media to another support media that has been impregnated with the reagent. For example, a strip of cellulose acetate as described above may be soaked or impregnated with triglyceride reagent. A sandwich of a strip of cellulose acetate impregnated with the reagent and the electrophoresed media is then made, which is incubated as described above.

Where the developing substrate is this enzymatic triglyceride reagent, the lipoprotein triglycerides are stained a reddish color and are easily visualized on the support media. Further, as described, the lipoprotein fractions have been separated during electrophoresis, permitting quantitative determination of the concentration of the high density lipoprotein, very low density lipoprotein and low density lipoprotein triglycerides.

Quantitation may be accomplished by one of several methods. In the simplest method, the support media is scanned by a suitable instrument for measuring absorbence, such as a densitometer. Alternatively, the individual fractions may be eluted and the absorbence measured by a Spectrophotometer. As will be understood by those skilled in the art, other quantitative methods may also be utilized. For example, the triglycerides may be tagged with fluoroescence or a radioactive isotope, such as iodine 125. Where fluorescene is used, the concentration of each fraction may be determined by a fluorescent densitometry or spectrophotometry. Where a radioactive isotope is utilized, the concentrations are determined by measuring the radioactivity of each sample using a radioisotope scanner. Additionally, where a thin sheet or strip of cellulose acetate is used for the electrophoresis support medium, the individual lipoprotein fractions may be cut out with scissors. Then, each fraction may be dissolved and the fluorescence or radioactivity of each sample measured. This provides a very accurate determination.

It will be understood by those skilled in the art that various modifications may be made to the method of determining the concentration of lipoprotein triglycerides of this invention. Further, details of the electrophoretic method will be understood by those skilled in the art. For example, U.S. Pat. No. 4,005,434 discloses a method and apparatus for graphic densitometer display which may be used in the method of this invention.

I claim:

1. A method of simultaneously determining the concentrations of high density lipoprotein triglyceride, very low density lipoprotein triglyceride and low density lipoprotein triglyceride in a sample of body fluid, comprising the steps of:
    a. applying a small sample of said body fluid to be tested to a solid electrophoresis support media strip,
    b. applying a direct current for a predetermined period of time to said support media until the high density, very low density and low density lipoprotein triglycerides have separated on the media,
    c. applying a developing substrate sensitive to small concentrations of triglycerides to the electrophoresed lipoprotein strip, and
    d. quantitatively determining the concentrations of high density lipoprotein, very low density lipoprotein and low density lipoprotein triglycerides in said body fluid sample from the developed electrophoresed sample.

2. The method of determining concentrations of lipoprotein triglycerides in a sample body fluid defined in claim 1, wherein said developing substrate is an enzymatic triglyceride reagent which is applied to said electrophoresis support media.

3. The method of determining concentrations of lipoprotein triglycerides in a sample of body fluid defined in claim 2, wherein said triglyceride reagent is applied to said support media by immersing the media in a fluid sample of said triglyceride reagent.

4. The method of determining concentrations of lipoprotein triglyceride in a sample of body fluid defined in claim 2, wherein said enzymatic triglyceride substrate is applied to said support media by impregnating an untreated strip of support media with fluid triglyceride reagent and applying said impregnated strip to the electrophoresed lipoprotein triglycerides in a sandwich form and incubating the sandwiched media for a predetermined period of time.

5. The method of determining concentrations of lipoprotein triglyceride in a sample of body fluid defined in claim 1, wherein said electrophoresis support media is cellulose acetate and said direct current is about one hundred eighty (180) volts which is applied to said support media for about twenty minutes.

6. The method of determining concentrations of lipoprotein triglycerides in a sample of body fluid defined in claim 1, wherein the concentrations of the lipoprotein triglycerides are quantitatively determined by a densitometer by measuring absorbance of each lipoprotein triglyceride following application of the developing substrate.

7. The method of determining concentrations of lipoprotein triglyceride in a sample of body fluid defined in claim 1, wherein said quantitative determination is made by eluting each electrophoresed fraction, including high density lipoprotein, very low density lipoprotein and low density lipoprotein triglyceride and then quantitatively determining the concentration of each fraction.

8. The method of determining concentrations of lipoprotein triglycerides in a sample of body fluid defined in claim 7, wherein the concentration of each fraction is determined using a spectrophotometer.

9. The method of determining concentrations of lipoprotein triglycerides in a sample of body fluid defined in claim 7, wherein said triglyceride reagent is tagged with fluorescene, including quantitatively determining the concentration of each fraction by measuring the fluorescence.

10. The method of determining concentrations of lipoprotein cholesterols in a sample of body fluid defined in claim 7, wherein said triglyceride reagent is tagged with a radioactive isotope, including quantitatively determining the concentration of each fraction by measuring the radioactivity of each fraction with a radioisotope counter.

11. A method of determining the concentration of high density lipoprotein triglyceride in body fluid, comprising:
   a. applying a small sample of said body fluid to a solid electrophoresis support media,
   b. applying a direct current across said electrophoresis support media until the high density lipoprotein triglyceride has separated from any remaining lipoprotein in said sample,
   c. applying a developing substrate sensitive to high density lipoprotein triglycerides to the separate electrophoresed high density lipoprotein triglyceride, and
   d. quantitatively determining the concentration of the high density lipoprotein triglyceride present in said body fluid from said developed electrophoresed sample.

12. The method of determining the concentration of high density lipoprotein triglyceride in a fluid sample defined in claim 11, wherein said developing substrate is an enzymatic triglyceride substrate and said support media is cellulose acetate, including applying said triglyceride reagent to the electrophoresed sample on said cellulose acetate media.

* * * * *